United States Patent [19]

Mai et al.

[11] Patent Number: 4,902,831
[45] Date of Patent: Feb. 20, 1990

[54] PREPARATION OF ETHYLENEDIAMINE DERIVATIVES

[75] Inventors: Khuong H. X. Mai, Waukegan; Ghanshyam Patil, Vernon Hills, both of Ill.

[73] Assignee: E. I. Du Pont de Nemours & Co., Wilmington, Del.

[21] Appl. No.: 118,126

[22] Filed: Nov. 9, 1987

[51] Int. Cl.$^4$ .................. C07C 85/12; C07C 85/11; C07C 87/28
[52] U.S. Cl. .................. 564/367; 564/385; 564/494; 564/495
[58] Field of Search ............. 564/495, 494, 367, 385

[56] References Cited

U.S. PATENT DOCUMENTS

| | | | |
|---|---|---|---|
| 2,408,171 | 9/1946 | Johnson | 564/494 |
| 3,336,386 | 8/1967 | Dovell et al. | 564/494 |
| 3,886,193 | 5/1975 | Whitney et al. | 564/511 |
| 4,751,328 | 6/1988 | Yamaguchi et al. | 564/385 |

FOREIGN PATENT DOCUMENTS 0665631  5/1988  Switzerland .................. 564/385

*Primary Examiner*—Richard L. Raymond
*Assistant Examiner*—Raymond Covington

[57] ABSTRACT

Described is a process for preparing 1,2-diaminoethane having the formula

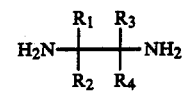

where $R_1$, $R_2$, $R_3$, and $R_4$ are each independently hydrogen, $C_1$–$C_{20}$ alkyl, $C_3$–$C_{12}$ cycloalkyl, $C_7$–$C_{15}$ aralkyl, unsubstituted or substituted aryl or heteroaryl or alternatively, $R_1$ and $R_2$ together with the carbon atom form a 3 to 12 member cycloalkyl group, or with a heteroatom form a 3 to 12 member heterocyclic group and $R_3$ and $R_4$ together with the nitrogen atom form a 3 to 12 member heterocyclic group, optionally including oxygen, sulfur or phosphorus as a second heteroatom, the process comprising: reacting a preformed Schiff base with a nitroalkane as a neat mixture in the presence of a catalytic amount of an inorganic base to form the 1-nitro-2-aminoethane intermediate, which was then hydrogenated to give 1,2-diaminoethane.

3 Claims, No Drawings

PREPARATION OF ETHYLENEDIAMINE DERIVATIVES

BACKGROUND OF THE INVENTION 1,2-Diaminoethane is an important intermediate in the preparation of beta-blockers, thiadiazoles and imidazole derivatives. A number of methods describe the preparation of 1,2-diaminoethane but as yet, none provide a completely satisfactory procedure. A good procedure for the preparation of 1,2-diaminoethane system is reported in U.S. Pat. No. 2,408,171. In that procedure, 2-methyl-2-nitropropanol was allowed to react with 20 fold excess of liquid ammonia, and the resulting mixture was hydrogenated at 1100 psi to give 71% yeild of 2-methyl-1,2-diaminoethane.

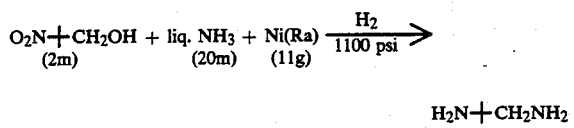

SUMMARY OF THE INVENTION

In accordance with one embodiment of the present invention, 1,2-diaminoethanes(4) were prepared by hydrogenating the 1-nitro-2-aminoethane intermediate(3); the latter was prepared by reacting a nitroalkane(1) with a N-benzyl imine(2) in the presence of a catalytic amount of an inorganic base.

The process of the invention can be depicted by the following reaction scheme.

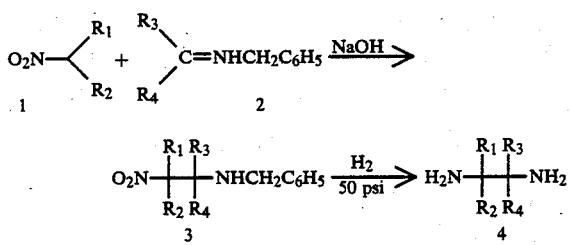

In the above scheme $R_1$, $R_2$, $R_3$ and $R_4$ are each independently hydrogen, $C_1$–$C_{20}$ alkyl, $C_3$–$C_{12}$ cycloalkyl, $C_7$–$C_{15}$ aralkyl, unsubstituted or substituted aryl or heteroaryl or alternatively, $R_1$ and $R_2$, $R_3$ and $R_4$, together with the carbon atom form a 3 to 12 member cycloalkyl group, or with a heteroatom form a 3 to 12 member heterocyclic group, optionally including oxygen, sulfur, or phosphorus to form a 3 to 12 member heterocyclic group.

The term "alkyl" as used herein refers to straight or branched chain alkyl radicals containing from 1 to 20 carbon atoms including but not limited to methyl, ethyl, n-propyl, iso-propyl, n-butyl, sec-butyl, t-butyl, 2-methylhexyl, n-pentyl, 1-methylbutyl, 2,2-dimethylbutyl, 2-methylpentyl, 2,2-dimethylpropyl, n-hexyl, heptyl, octyl, nonyl, decyl, or eicosyl and the like.

The term "cycloalkyl" as used herein refers to cyclic saturated aliphatic radicals containing 3 to 12 carbon atoms in the ring, such as cyclopropyl, cyclobutyl, cyclopentyl, cyclohexyl, or cyclododecyl.

The term "aryl" represents phenyl or naphthyl which may be unsubstituted for substituted with loweralkyl of from 1 to about 6 carbon atoms, halo, hydroxy, amino, nitro, loweralkoxy, carboxy, loweralkanoyl, or loweralkoxycarbonyl.

"Heteroaryl" as used herein refers to radicals such as thiophene, furan, pyridine or imidazole, which may be unsubstituted or substituted.

"Substituted aryl or heteroaryl" as used herein referes to aryl or heteroaryl substituted with loweralkyl, loweralkoxy, carboloweralkoxy, amido, or halo.

"Heteroatom" as used herein refers to atoms including oxygen, sulfur, nitrogen, or phosphorus.

In the process, a nitroalkane(1) is allowed to react with a N-benzyl imine(2) as a neat mixture in the presence of a catalytic amount of an inorganic base. A suitable temperature is 20° to about 125°, preferably 80° to about 100° and a reaction time of 10 minutes to 5 hours, preferably 30 minutes to 2 hours. The 1-nitro-2-aminoethane(3) so formed, was hydrogenated at about 1 psi to 200 psi of hydrogen, preferably 10 psi to 60 psi. to give the desired 1,2-diaminoethane(4). A suitable temperature is 20° to about 125°, preferably at ambient temperature and a reaction time of 2 hours to 24 hours, preferably overnight. Suitable solvents are water, methanol, ethanol, propanol, butanol, phenol, formic acid, acetic acid, or a mixture thereof providing that enough acid is added to the solution to neutralize any diamine so formed during the hydrogenation. Preferably, the pH of the solution should be less than 7 at the end of the hydrogenation.

The following scheme illustrates the use of 1,2-diamino compounds to synthesize various beta-adrenergic blocking compounds.

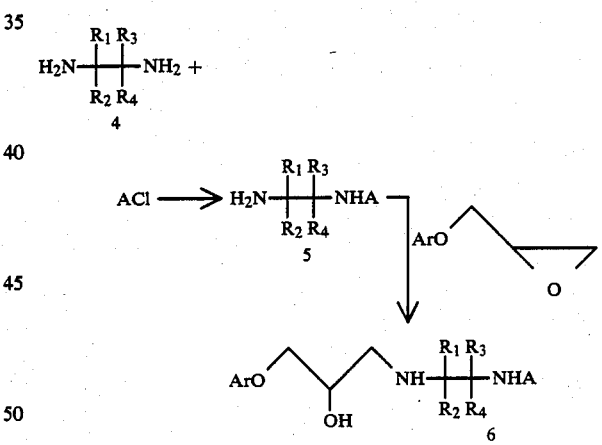

In the above scheme, A together with the nitrogen (AN) forms an amido (RCON), a carbamate (ROCON), a ureido (RRNCON), a sulfonamido ($RSO_2N$), or a sulfamido ($RRNSO_2N$).

By considering the preparation of the 1,2-diamino derivatives in the above scheme, one can perceive that the 1-nitro-2-benzylamine intermediate(3) offers an alternative route for the preparation of 1,2-diamno derivatives(5) as depicted in the following scheme:

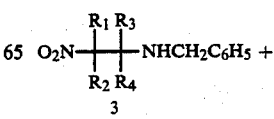

-continued

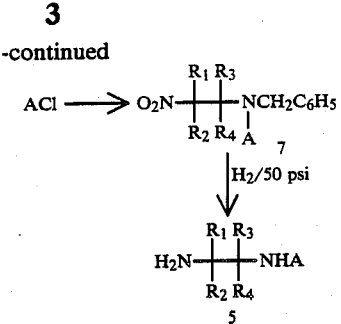

In fact, the derivatization by this methodology yields a N-monosubstituted compound as the only product, whereas the derivatization of the diamine(4), although it also provides the desired N-monosubstituted derivative(5), is always contaminated with a small amount of N-N-disubstituted compound.

DETAILED DESCRIPTION OF THE INVENTION

In accordance with one embodiment of the present invention, the preparation of 1,2-diaminoethane systems was conducted as follows.

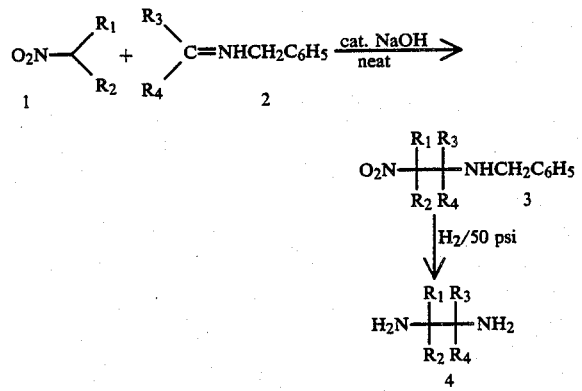

In general, the 1,2-diamino compounds are converted into the corresponding derivatives prior to condensation with an epoxide to produce the desired beta-blockers.

The following scheme illustrates the use of 1,2-diamino compounds to synthesize various beta-blockers,

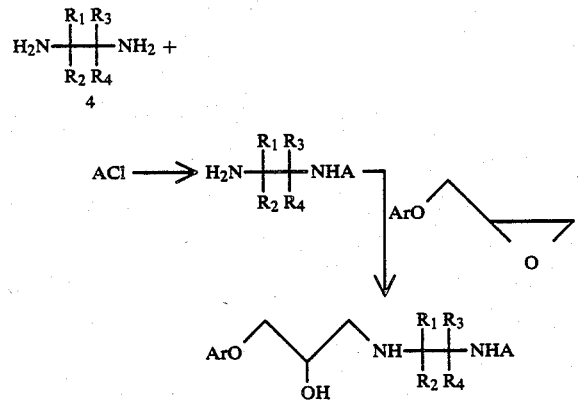

wherein A is an acid radical. A together with the nitrogen (N—A) forms an amido (N—COR), a carbamate (N—COOR), a ureido (N—CONRR), a sulfonamido (N—SO$_2$R) or a sulfamido (N—SO$_2$NRR) group.

By considering the preparation of the 1,2-diamide derivatives(5) in the above scheme, one could perceive that the 1-nitro-2-benzylaminoethane(3) in the previous scheme offers an alternative route for the preparation of 1,2-diamino derivatives. The intermediate, 2-nitro-2-benzylaminoethane(3), provides an exclusive selectivity for many reactions on the amino group as shown in the following scheme:

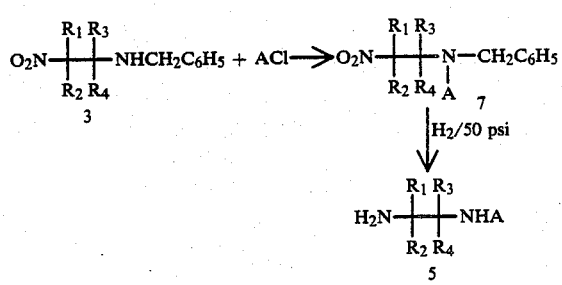

In fact, the derivatization by this methodology yields a N-monosubstituted compound as the only product whereas the derivatization of the diamine, although it also gives the desired N-mono substituted derivative, is always contaminated with a small amount of N,N-disubstituted compound.

EXAMPLE 1

Preparation of N-Benzyl 2-nitro-2-methyl-propylamine, HCl

A mixture of 2-nitropropane (107 g; 1.2 mole), N-benzyl formaldimine (120 g, 1.0 mole), and sodium hydroxide (1 g) was heated to reflux for 2 hours. The reaction mixture was cooled to an ice bath, acidified with 100 ml of concentrated hydrochloric acid (1.2 mole). The slurry mixture was mixed with 200 ml of methyl isobutyl ketone and evaporated to almost dryness. The procedure was repeated twice more to azeotrope most of the water. The solid residue was mixed with 300 ml of methyl ethyl ketone, heated and vigorously stirred to break up any lumpy material. After cooling to about 10°–15° C., the thick slurry mixture was diluted with methyl isobutyl ketone and filtered. Yield, 195 g (79.7%), m.p. 182°–184° C., spectrum data are consistent with the assigned structure.

For analytical purpose, a small amount of the KCl salt was recrystallized from methyl ethyl ketone, mp. 187°–188° C.

The HCl salt is fairly soluble in water, alcohol, acetone, 2-nitropropane, slightly soluble in methyl ethyl ketone, ethyl acetate, insoluble in methyl isobutyl ketone.

EXAMPLE 2

Preparation of 2-methyl-1,2-diaminopropane

Method 1 - A mixture of 2-nitropropane (54 g; 0.6 mole), N-benzyl formaldimine (60 g; 0.5 mole), and sodium hydroxide (1 g) was heated to reflux for 2 hours. The reaction mixture was cooled in an ice bath, diluted with 500 ml of methanol, acidified with 100 ml of concentrated hydrochloric acid, added with 5 g of 10% Pd/C, hydrogenated at 50 psi at room temperature overnight. After filtration, the filtrate was evaporated to dryness and the residue was evaporated with ethyl acetate to remove trace of water. The solid residue was treated with 200 ml of 25% sodium methoxide in methanol and the slurry mixture was distilled at atmospheric pressure to give the title compound as a clear oil, 30 g (68.2%), b.p. 125°–135° C.

The dihydrodiloride salt has a melting point of 300° C. and the monohydrochloride salt melts at 195° C. The pHs of their aqueous solution are 3 and 9, respectively.

EXAPMLE 3

Preparation of 2-methyl-1,2-diaminopropane

Method 2 - A mixture of N-benzyl 2-nitro-2-methylpropylamine hydrochloride (42 g, 0.2 mole), methanol (300 ml), acetic acid (15 ml), and 10% Pd/C (3 g) was hydrogenated at 50 psi of hydrogen at room temperature overnight. The mixture was filtered, acidified with 17 ml of concentrated hydrochloride, and evaporated to dryness. The residue was mixed with 200 ml of methyl isobutyl ketone and the mixture was evaporated to remove any trace of water. The solid residue was added with 25% sodium methoxide in methanol (88 g, 0.4 mode) and the mixture was distilled to give 13 g (73.8%) of the titled compound, bp. 125°–132° C.

EXAMPLE 4

Preparation of N-(2-amino-2-methyl)propyl benzamide

To a mixture of N-benzyl 2-nitro-2-methylpropylamide hydrochloride (49 g, 020 mole), triethylamine (22.2 g, 0.22 mole), THF (300 ml) was added dropwise benzoyl chloride (29.5 g, 0.21 mole). At the end of the addition, the mixture was heated to reflux for 30 minutes, cooled in an ice bath, and filtered. The filtrate was mixed with acetic acid (10 ml), 10% Pd/C (2 g), and hydrogenated at 50 psi of hydrogen at room temperature overnight. The mixture was filtered and the filtrate was evaporated to dryness. The residue was mixed with 200 ml of methyl isobutyl ketone and evaporated to remove any trace of water. The semi-solid residue was basified with 25% sodium methoxide in methanol (44 g, 0.2 mole) and evaporated to dryness. Tetrahydrofuran (200 ml) and magnesium sulfate (20 g) was added to the mixture. After filtration, the solvent was removed to give a solid, which was recrystallized from isopropyl ether-isopropyl alcohol mixture to yeild 15 g (19.5%) of the title compound, mp 83°–86° C.; spectrum data are consistent, with the assigned structure.

What is claimed is:

1. A process of preparingn a derivative of a 1,2-diamioethane of the formula

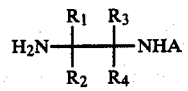

wherein $R_1$, $R_2$, $R_3$ and $R_4$ are each independently hydrogen, $C_1$–$C_{20}$ alkyl, $C_3$–$C_{12}$ cycloalkyl, $C_7$–$C_{15}$ aralkyl, unsubstituted or substituted aryl or heteroaryl, or alternatively, R1 and R2, $R_3$ and $R_4$ together with the carbon atom to which they are attached form a 3 to 12 member cycloalkyl group, or with a heteroatom form a 3 to 12 member heterocyclic group, optionally including oxygen, sulfur, or phosphorus as the heteroatom, and A together with N forms an amido, a carbamate, an ureido, a sulfonamido, or a sulfamido group, which process comprises: reacting and acid radical halide (AX) with a N-benzyl 2-nitropropylamine to produce the intermediate N-benzyl N-substituted 2-nitropropylamine; hydrogenating the compound so formed at medium pressure using Pd/C as a catalyst to produce the N-substituted derivatives of 1,2-diaminoethanes.

2. The process of claim 1 wherein the reaction temperature ranges from about 25° to 125° C. for a time of about 24 hours.

3. The process of claim 2 wherein the hydrogenation pressure ranges from about 1 psi to 90 psi.